United States Patent [19]
Novick

[11] Patent Number: 5,195,973
[45] Date of Patent: Mar. 23, 1993

[54] SELF-DESTRUCTING DISPOSABLE SAFETY SYRINGE SYSTEM WITH PISTON AND PLUNGER JOINED BY WEAK ATTACHMENT SEALANT

[76] Inventor: Howard J. Novick, 1474 Sugar Creek Blvd., Sugarland, Tex. 77478

[21] Appl. No.: 839,943

[22] Filed: Feb. 21, 1992

[51] Int. Cl.5 ............... A61M 5/50; A61M 5/315
[52] U.S. Cl. ............................. 604/110; 604/228
[58] Field of Search ............... 604/110, 192, 263, 218, 604/220, 228, 195

[56] References Cited

U.S. PATENT DOCUMENTS

| | | | |
|---|---|---|---|
| 3,245,567 | 4/1966 | Knight | 215/42 |
| 3,333,682 | 8/1967 | Burke | 604/192 |
| 4,248,246 | 2/1981 | Ikeda | 128/765 |
| 4,391,272 | 7/1983 | Staempfli | 604/110 |
| 4,493,703 | 1/1985 | Butterfield | 604/110 |
| 4,643,199 | 2/1987 | Jennings, Jr. et al. | 128/763 |
| 4,654,034 | 3/1987 | Masters et al. | 604/192 |
| 4,775,364 | 10/1988 | Alles | 604/110 |
| 4,883,470 | 11/1989 | Haindl | 604/192 |
| 4,923,443 | 5/1990 | Greenwood et al. | 604/110 |
| 4,932,941 | 6/1990 | Min et al. | 604/110 |
| 4,950,243 | 8/1990 | Estruch | 604/110 |
| 5,047,017 | 9/1991 | Koska | 604/110 |
| 5,106,372 | 4/1992 | Runford | 604/110 |
| 5,135,495 | 8/1992 | Arcusin | 604/110 |

Primary Examiner—John D. Yasko
Assistant Examiner—Adam J. Cermak
Attorney, Agent, or Firm—Joseph J. Kaliko

[57] ABSTRACT

A self-destructing disposable safety syringe system, suitable for preventing needle sticks, preventing syringe reuse, and dispensing fluids from, drawing fluids into and mixing fluids within the system. According to one embodiment of the invention, the system includes a cylinder having a nozzle on one end to which a syringe needle can be affixed and an at least partially resilient piston comprising a body arranged so as to form a liquid tight movable partition (suitable for sliding against the inside wall of said cylinder under the control of a force applied through an actuator rod attached to the piston); a safety cap for preventing needle sticks from any needle attached to the nozzle, where the safety cap has flared construction to ease the placement of said cap over the needle and further including a cap lock for preventing the accidental removal of the safety cap means once in place; a syringe locking mechanism, located on the interior wall of the cylinder and extending therein, for preventing the retraction of the piston once the piston is depressed beyond a certain predefined limit; and a self-destruct mechanism which causes the syringe to self destruct if any reuse attempt is made after the piston has been depressed beyond the predefined limit.

20 Claims, 3 Drawing Sheets

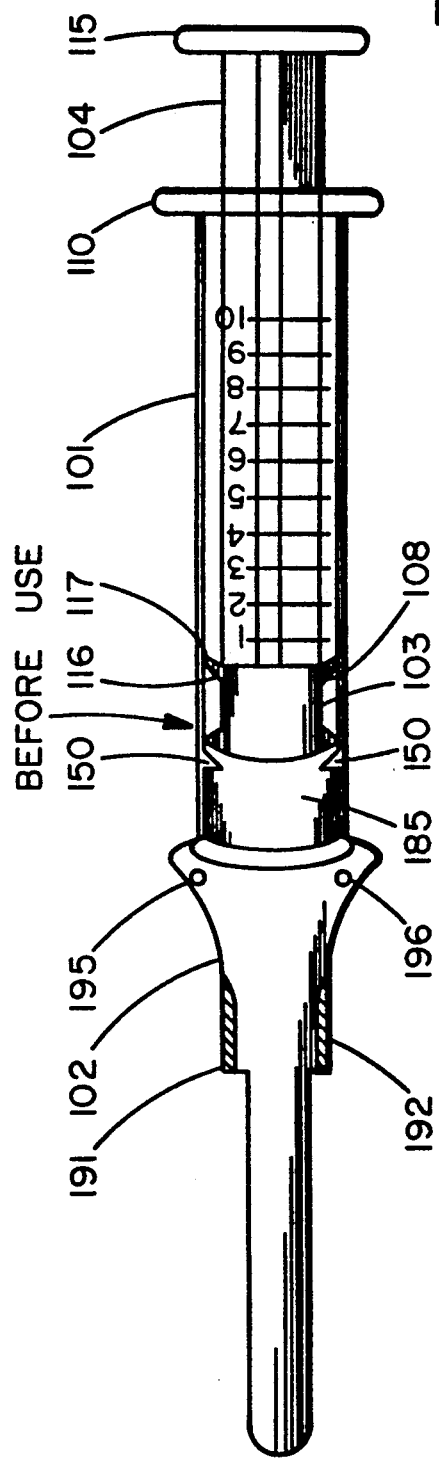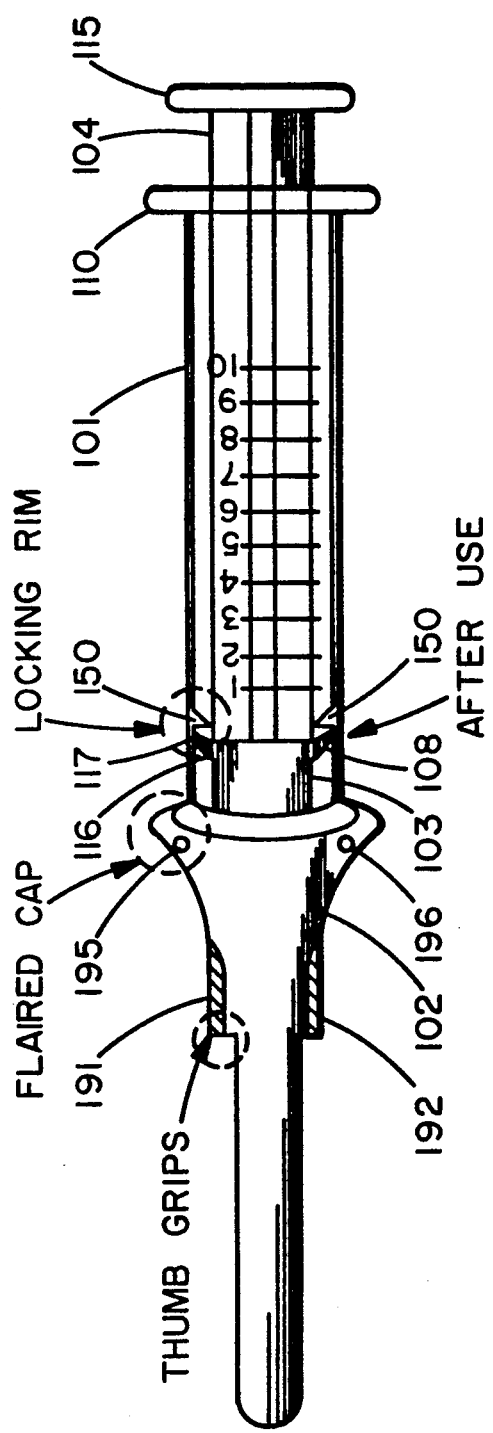

SELF-DESTRUCTING DISPOSABLE SAFETY SYRINGE SYSTEM WITH PISTON AND PLUNGER JOINED BY WEAK ATTACHMENT SEALANT

BACKGROUND OF THE INVENTION

1. Field of the Invention

The invention relates generally to the field of medical equipment, and more particularly relates to a self-destructing syringe system that incorporates safety improvements into hypodermic syringes that are used, for example, to administer injections or take blood samples. These improvements are designed to provide a single integrated safety syringe system which prevents the reuse of the syringe and at the same time protects medical personnel administering medications through the needle (or sampling bodily fluids using the syringe) from inadvertent contamination as a result of a "needle stick".

2. Description of the Related Art

There is presently and has for some time been a need to have low cost commercially available safety syringes which are disposable and cannot be reused. This is particularly true because a large number of injections of medicinal or other substances need to be carried out by patients themselves, that is to say, without the assistance of medical practitioners, under conditions which do not permit an effective sterilization of the syringe before it is used. Even where medical practitioners are available to administer injections, disposable, self-destructing devices are desirable to prevent the reuse of syringes by, for example, individuals addicted to drugs who might utilize such devices discarded as medical waste.

While single use disposable devices are well known which do protect patients from the danger of infectious diseases, such as AIDS and certain hepatitis viruses, they are not known to be included in combination with, nor are they part of, a single integrated low cost safety syringe system which includes (1) efficient means for allowing fluids to be mixed in the syringe prior to the delivery of an injection; along with (2) effective means for protecting medical and hospital personnel from infection due to accidental contact with a contaminated needle or other portion of the disposable apparatus.

For example, hypodermic needles are usually equipped with a removable cap that protects and helps keep the needle sterile. The cap is usually replaceable to cover the used, contaminated needle and prevent accidental needle sticks. However, accidental needle sticks during recapping have long been a problem. Because of tension, time pressure, or fatigue, needle sticks during recapping occur with alarming frequency despite frequent warnings to be careful, and they account for the majority of accidental needle sticks.

Eliminating recapping will not solve the problem because the uncapped needle is so dangerous. Indeed, a large number of accidental needle sticks are caused by uncapped needles found in beds, on floors, or in garbage cans. Even where there is a no recapping policy, the needles are often recapped because of these dangers.

Accidental needle sticks are serious because they can spread disease, including hepatitis, venereal diseases, and of most recent concern: AIDS. A needle stick causes fear and anxiety in the victim. Both the victim and the patient may be subjected to a battery of expensive, time consuming tests. Accidental needle sticks during recapping can cost even a relatively small health care institution thousands of dollars annually. Even worse than the economic cost, however, is the transmission of disease.

For example, the victim of a needle stick from a needle contaminated by an AIDS patient must be repetitively tested for several months after the accident. It is documented that after such a needle stick, the victim may test positive for exposure to the AIDS virus, even if the disease is not contracted. A positive test would cause great fear and anxiety in the victim, would seriously disrupt the victim's personal life, and might even end a victim's ability to work in health care.

Despite the very serious nature of the problem, and the severity of the consequences, the problem has persisted for many years without any satisfactory solution.

Various sheaths that can be slid down over the needle after use have been patented, for example those disclosed in U.S. Pat. No. 4,425,120, U.S. Pat. No. 3,780,734 and U.S. Pat. No. 2,571,654. However, these devices are to complicated, and to difficult and expensive to manufacture, and have never been widely available.

Masters et al, in U.S. Pat. Number 4,654,034, issued Mar. 31, 1987, proposed a safety needle cap comprising a generally cylindrical, hollow tubular body section having a closed first end and an open second end for receiving the needle, and a funnel-shaped lip surrounding the open end and projecting radially and axially outwardly to channel needles into the open end and protect fingers gripping the cap. The cap taught by Masters et al also includes a guard to space fingers away from the open end. The flared ends of the cap and the guard are designed to protect against needle sticks.

In addition to Masters et al, Jennings, Jr. et al, in U.S. Pat. No. 4,643,199; Burke in U.S. Pat. No. 3,333,682; and Ikeda, in U.S. Pat. No. 4,428,246, all disclose needle covers having flared open ends to help protect against needle sticks. However, none of the improvements taught by the aforementioned patents are taught in combination with or as part of an integrated self destructing safety syringe system which simultaneously protects the syringe user from accidental needle sticks, allows for fluids to be mixed in the syringe system prior to delivery, etc.

Knight, in U.S. Pat. No. 3,245,567, is representative of prior art which teaches the use of thumb grips on a sterilized needle storage container using a flared needle cover to give additional protection against accidental needle sticks when sealing the container. However, Knight does not teach the use of a flared needle cap with thumb grips as part of a safety syringe system, nor does Knight address the other desirable aspects of an integrated safety system as mentioned hereinabove, namely the ability to perform fluid mixtures within utilizing the syringe system, self-destruction of the syringe after use, etc.

Syringes intended for being used only for a single injection are also known. For example, French patent application no. 76 12 199 describes a combined ampoule and syringe, in which a piston carries, at its end placed inside the cylinder of the syringe, a joint which is separable from the piston, which is designed to remain in its final position at the bottom of the cylinder when the injection has been carried out. A retraction of the rod causes a separation between the rod and the joint of the piston.

The syringe described in the aforementioned French Patent Application does not, however, permit a liquid to be drawn in from an ampoule. On the other hand, in the construction as proposed by the French Patent Application, it would be an easy matter to remove the joint or packing of the cylinder from the syringe by other means and to use the syringe again after having refilled it.

German patent application no. 17 66 748 proposes a syringe in which the rod is provided with a locking device for preventing the return of the piston from a position of maximum insertion. Nevertheless, this arrangement, situated outside the cylinder, can be easily detached or made inoperative, so that this syringe does not give any guarantee for it not to be used again.

An effectively disposable syringe is described in French patent application no. 75 15 412. It comprises means associated with that part of the piston which is disposed inside the cylinder; but permitting only a single intake and ejection movement of the piston.

As indicated hereinabove, it is frequently necessary to effect the injection of a mixture of several different liquid substances, which mixture cannot be prepared in advance, but only at the moment of injection. This involves the necessity of having available a syringe which is capable of being filled in several steps, that is to say, a syringe of which the piston can carry out an indefinite number of reciprocating movements during the filling of the cylinder before the operation of injection.

Staempfli in U.S. Pat. No. 4,391,272, issued Jul. 5, 1983, addresses the problem of mixing liquids in a disposable syringe prior to injection by proposing a syringe comprising a cylinder of which one end is provided with a nozzle permitting the fixation of a needle, an intake and delivery piston comprising a body arranged so as to form a tight movable partition capable of sliding inside the cylinder, a rod fast with the body of the piston and permitting the latter to be displaced with a sliding movement in the cylinder, and means, cooperating with a groove that is cut or otherwise formed in the body of the cylinder, for preventing the rearward return of at least a part of the body of the piston when the said body occupies a position close to its position of maximum insertion into the cylinder.

In particular, Staempfli proposes several alternate embodiments of a syringe system which is disposable and addresses the problem of mixing liquids within the system; however, all of the embodiments taught by Staempfli require the cylindrical body portion of the system to have a groove formed therein for either (1) engaging the rim of the piston to prevent withdrawal of the piston and reuse of the syringe; (2) retaining a detachable 0-ring sealing joint fitted onto the piston body during the manufacturing process; or (3) receiving a disengagable packing or sealing joint fitted onto the piston body during the manufacturing process.

It would be desirable to have a safety system that includes the benefits of the system described by Staempfli, i.e., one that is disposable and which allows for the mixing of fluids within the system. However, it would also be desirable if such a system did not have to rely upon costly and tolerance sensitive manufacturing processes associated with forming Staemplfi's grooves within the syringe cylinder bodies. For example, the reuse prevention mechanism taught by Staempfli, namely the grooves into which the various deformable members must fit and be retained, can be easily defeated if not manufactured to precise specifications which allow the deformable members to be accepted and held therein.

Finally, Butterfield in U.S. Pat. No. 4,493,703, issued Jan. 15, 1985, teaches a hypodermic cartridge with a drive piston rendered non-retractable by including on it a resilient disc-like element, having a diameter slightly larger than the glass tubular body of the syringe, which acts as a continuous pawl. Any attempt to retract the drive piston jams the edge of the resilient element against the inside wall of the tubular body.

Although providing means for preventing retraction of a piston within a syringe, Butterfield is expressly directed to syringe systems which are not capable of solving the aforementioned fluid mixing problem. It is in this context that the Butterfield invention is described and in fact Butterfield's preferred syringe cartridge (which does not permit fluid mixing) utilizes a detachable actuator rod/piston assembly to assure piston non-retractability.

Moreover, all the preferred embodiments of the invention illustrated in the Butterfield patent teach a threaded actuator rod simply fitted over an unthreaded shank portion of the piston to assure detachment of the actuator rod if an attempt is made to retract the piston at any time. Such an arrangement is incompatible with syringe systems that provide for the desirable capability of mixing of fluids, as, for example, the system taught by Staempfli.

It should be noted that a "less preferred" embodiment of the Butterfield invention disclosed in U.S. Pat. No. 4,493,703, as an aid against piston retractability when the actuator rod and the piston are actually attached to one another, relies on the inside surface of the tubular member portion of the syringe including a number of longitudinally spaced ratchet teeth to engage the resilient disc. This arrangement, although designed to prevent retraction of the piston, is characterized by Butterfield as (1) being difficult to manufacture and (2) less preferred then embodiments that have the actuator rod sitting on the unthreaded shank, since the disc like elements contemplated by Butterfield, in Butterfield's words, "could probably be overpowered by the application of brute force on a fixedly attached piston".

Accordingly, since the Butterfield syringe is not compatible with devices that are used to mix fluids; does not teach the aforementioned desirable needle stick prevention safety features; does not teach these features in combination with a syringe that has an inherent self destruct capability to prevent reuse (for example, Butterfield's detachable actuator rod can be reseated on the piston assembly effectively reconnecting it thereto when an unthreaded shank is used on the piston); and is admittedly difficult to manufacture, it would be desirable to provide a self destructing safety syringe system that solves all of the aforementioned problems inherent in not only Butterfield, but in all of the known prior art syringe systems, whether taken individually or combined.

SUMMARY OF THE INVENTION

Thus, it is an object of the invention to provide a self destructing safety syringe system which prevents needle sticks and syringe reuse.

It is a further object of the invention to provide a self destructing safety syringe system which facilitates both administering injections and the withdrawal of fluids for sampling and/or mixing purposes.

It is a still a further object of the invention to provide a self destructing safety syringe system which realizes the aforementioned objectives and is both low in cost and easy to manufacture.

According to one aspect of the invention, a self-destructing disposable safety syringe system, suitable for expelling fluids from, drawing fluids into and mixing fluids within said system, is disclosed which comprises: (a) a cylinder having a nozzle on one end to which a syringe needle can be affixed; (b) an at least partially resilient piston, suitable for sliding against the inside wall of said cylinder under the control of a force applied though an actuator rod attached to said piston, comprising a body arranged so as to form a liquid tight movable partition; (c) an actuator rod, connected to said piston via a weak attachment (to be defined hereinafter), for controlling the displacement of said piston within said cylinder by the application of forces through said actuator rod; and (d) a syringe locking mechanism, located on the inside wall of said cylinder and extending therein, arranged to permit the passage of said piston in the direction of said needle when forced in said direction by said actuator rod, and further arranged to engage and inhibit the passage of said piston in the direction away from said needle only once the entire piston has been forced past said syringe locking mechanism, thereby accommodating any desired expelling of fluids from, drawing of fluids into and mixing of fluids within the syringe system until such time as said locking mechanism is engaged.

The "weak attachment" referred to hereinabove is defined herein to mean an attachment of two components that will break, separate or otherwise give way under a predetermined amount of stress causing the components that were attached to become separated.

According to a further aspect of the invention, in fact a preferred embodiment thereof, the weak attachment between said actuator rod and said piston is formed by directly coupling said actuator rod to said piston utilizing a sealant. The forming of a combined actuator rod/piston in this manner reduces manufacturing costs and improves system reliability compared to prior art systems employing three or more indirectly coupled components (such as shown and taught in the aforementioned Butterfield reference which requires an insert be disposed between the actuator rod and piston), to fabricate a self-destructing safety syringe system as contemplated herein.

A further aspect of the invention is the inclusion in the safety system of a protective safety cap including a flared open end having a diameter that is greater than or equal to the body said cylinder and means for locking said protective safety cap in a position covering the needle to prevent inadvertent cap removal and accidental needle sticks.

According to an illustrative embodiment of the invention, the piston is shaped to include in one integral piece (or, in alternate illustrative embodiments, two or more piston pieces held together fast with, for example, a sealant that is stronger than the one used to form the aforementioned weak attachment of the piston and actuator rod), a resilient assembly member with a free end that has a circumferential portion that is flared (or which has a tendency to become flared when a force is exerted onto the free end through the depression of the actuator rod), forming a collar having a peripheral rim. Because of the elasticity of the resilient collar, the rim has a tendency to bear against the inside wall of cylinder forming a desired fluid tight partition within the cylinder and providing a means for engaging the aforementioned syringe locking mechanism should an attempt be made to retract the piston after it has been depressed beyond the point where the syringe locking mechanism is located. Any attempt to retract the piston after the syringe locking mechanism is engaged will cause the weak attachment to separate, effectively causing the syringe to self-destruct.

The syringe system contemplated by the invention features a simple actuator rod/piston assembly that is easily manufactured to include the desired "weak" connection between these combined components (the rod and piston) by, for example, simply utilizing a sealant between the adjoining faces of the actuator rod and the piston. Furthermore, the syringe system contemplated by the invention features the ability to dispense, draw and mix fluids while at the same time providing protection against accidental needle sticks and preventing syringe reuse via the system's inherent self-destruct capability.

These and other objects and features of the present invention and the manner of obtaining them will become apparent to those skilled in the art, and the invention itself will be best understood by reference to the following detailed description read in conjunction with the accompanying Drawing.

DESCRIPTION OF THE DRAWINGS

FIGS. 1A and 1B depict general side elevational views of an illustrative embodiment of the self-destructing disposable safety syringe system contemplated by the invention (including a partial sectional view of a thumb grip).

DETAILED DESCRIPTION

Figure 2:
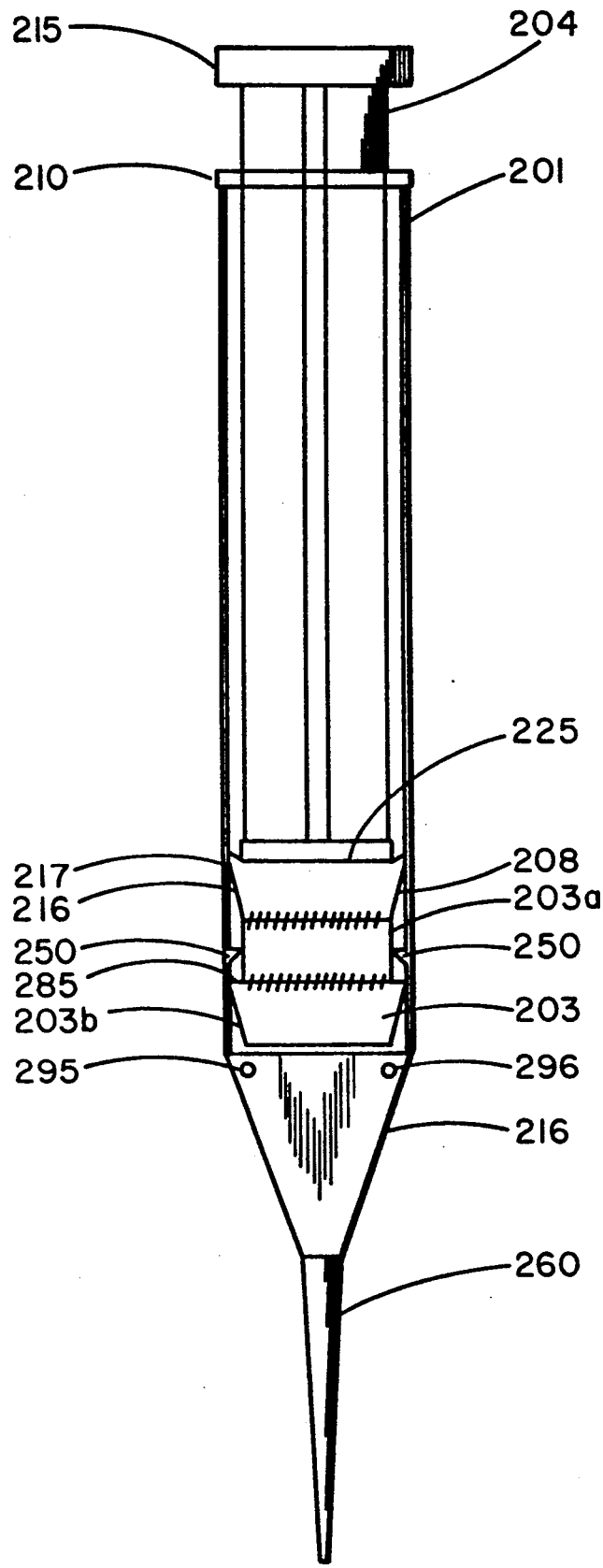
FIG. 2 is a simplified longitudinal cross-sectional view of the syringe system depicted in FIGS. 1A and 1B, with the flared safety cap removed and the piston shown partially depressed, i.e., with the syringe in use prior to the depicted locking mechanism being engaged.

The syringe system which is shown in FIGS. 1A and 1B, comprises a tubular cylinder 101 (sometimes referred to herein as the syringe barrel), one end of which is formed with a nozzle located under flared cap 102 (the nozzle is not shown in FIG. 1; but is depicted in FIG. 2 to be described hereinafter), permitting an injection needle to be fixed thereon, and an intake and delivery piston which consists of a body 103 forming a tight movable partition which is capable of sliding while maintaining the tightness, along the inside wall of cylinder 101, and a piston rod (sometimes referred to herein as an actuator rod) 104. The cylinder 101, the body 103 and the piston rod 104 may, for example, be formed by synthetic resin.

Flared cap 102, for the purposes of illustration only, may be of the type described by Masters et al in the previously referenced U.S. Pat. No. 4,654,034, hereby incorporated by reference. The flared cap contemplated by the invention, however, is modified, according to a preferred embodiment, to allow the cap to be snap locked onto syringe barrel 101 once the syringe is used and the cap is placed over the needle.

An example of such a modified cap is shown in FIGS. 1A and 1B. Several apertures, such as the ones shown at 195 and 196 of FIGS. 1A and 1B, could, for example, be formed in the flared cap 102, to engage a pair of corresponding "snap lock" nubs (shown in FIG. 2 at 295 and 296) formed on nozzle 216 (also shown in FIG. 2). This feature would prevent the inadvertent removal of the cap and aid in preventing accidental needle sticks.

Furthermore, according to a preferred embodiment of the invention, flared cap 102 includes a thumb grip mechanism (shown at 191 and 192 in FIGS. 1A and 1B), which provides a means for safely gripping the cap between, for example, the user's thumb and forefinger. The use of such a mechanism on a flared needle cover (although not teaching such use in connection with a syringe system as contemplated herein), is, as indicated hereinbefore, suggested by Knight in U.S. Pat. No. 3,245,567, hereby incorporated by reference only for its teaching of a thumb grip on a flared cap.

Referring again to FIGS. 1A and 1B, that end of cylinder 101 which is opposite the nozzle (i.e., opposite flared cap 102), carries a collar in the form of a flat ring 110 as means for gripping and actuating the syringe; while the end of the piston rod 104 outside the cylinder 101 is shown provided with a disc 115 forming an integral part of the rod 104, thus also serving as gripping and actuating means.

The end of the actuator rod 104 which is disposed inside the cylinder 101 of the illustrative syringe system shown in FIGS 1A and 1B, is shown directly attached to an assembly member 108 which is integral with the body 103 of the piston. According to one aspect of the invention, this connection may be formed by any type of commercially available sealant (with adhesive properties) which creates a "weak attachment" between actuator rod 104 and the assembly member 108 portion of piston 103. As previously indicated, a "weak attachment" is defined to mean an attachment of two components (such as actuator rod 104 and the assembly member 108 portion of piston 103) that will break, separate or otherwise give way under a predetermined amount of stress (such as stress resulting from the application of opposing forces), causing the components that were attached to become separated. An example of how such a stress (or force) could be applied to actuator rod 104 and the free end of assembly member 108 (forming a part of piston 103), utilizing the syringe system contemplated by the invention, will be described in detail hereinafter.

The actuator rod 104/piston 103 combination (formed after the aforesaid attachment of these components during the syringe manufacturing process) is, according to the illustrative embodiment of the invention, utilized to displace piston 103 in cylinder 101 by action applied to actuator rod 104. The syringe depicted in FIGS. 1A and 1B may, via the actuator rod/piston combination, be utilized to inject fluids and/or draw fluids for mixing or sampling purposes (to or from well 185 shown in FIG. 1A) at any time before the locking mechanism contemplated by the invention is engaged. In other words, prior to piston 103 becoming engaged by the syringe locking mechanism 150 which is depicted in both FIGS. 1A and 1B. The operation of syringe locking mechanism 150 in cooperation with piston 103 and rod 104, will also be described in detail hereinafter.

In the illustrative embodiment of the invention depicted in FIGS. 1A and 1B, the assembly member 108 is shown in one piece with piston 103. This piece is preferably made of a resilient material which has a certain elasticity, for example, a synthetic plastic material, in order to ensure the aforementioned tight fit while allowing a sliding action between the piston 103 and the inside wall of cylinder 101. However, in an alternate embodiment, the body 103 of the piston could be made of a relatively hard material, in which case only a separate assembly member 108, held fast with the rest of piston 103, need be formed of the resilient material.

The free end of illustrative assembly member 108 (as shown in FIGS. 1A and 1B), in accordance with one embodiment of the invention, has a circumferential portion that is flared (or alternatively which has a tendency to become flared when a force is exerted onto the free end of assembly member 108 through the depression of actuator rod 104), forming a collar 116 which has a peripheral rim 117. Because of the elasticity of collar 116, the rim 117 has a tendency to bear against the inside wall of cylinder 101.

According to a further aspect of the invention, the inside wall of cylinder 101 (as shown in FIGS. 1A and 1B), is formed to include a syringe locking mechanism 150 which, for example, is depicted in the Drawing as a ridge extending inwardly and around the interior of cylinder 101. Alternatively, syringe locking mechanism 150 could, for example, include a set of locking teeth extending into the interior of cylinder 101. Independent of the specific form that syringe locking mechanism 150 takes, its function, should any attempt be made to retract the actuator rod/piston combination after the entire piston passes the portion of cylinder 101 where syringe locking mechanism 150 is located, is to engage rim 117 of piston 103.

In other words, only a "one way" passage of the piston 103, past syringe locking mechanism 150, is contemplated. The piston 103 shown in FIG. 1A (the "before use" diagram) may be forced past syringe locking mechanism 150 by use of actuator rod 104; but it is not possible for piston 103 to pass back to the right in cylinder 101 (past syringe locking mechanism 150) once the piston 103 is to the left of syringe locking mechanism 150 as shown in FIG. 1B (the "after use" diagram).

Syringe locking mechanism 150 would typically be fabricated within cylinder 101 at a predetermined location which would allow the syringe to be utilized for mixing fluids, as well as dispensing fluids, prior to being engaged. Accordingly, the preferred embodiment of the invention contemplates syringe locking mechanism 150 being located nearest the end of cylinder 101 opposite actuator rod 104, allowing sufficient cylinder volume between syringe locking mechanism 150 and the nozzle to which the needle is attached, to permit the at least partially resilient piston 103 to be compressed (by force exerted through the actuator rod 104); in turn enabling rim 117 to engage the locking mechanism after the syringe has been used should any attempt be made to retract the actuator rod/piston assembly.

Should an attempt be made to retract the actuator rod/piston assembly, the syringe system contemplated by the invention is designed to self-destruct. A force applied to the actuator rod 104/piston 103 combination, once piston 103 is situated as shown in FIG. 1B, will cause an opposing force to be exerted against collar 116 via the interaction of collar 116 and rim 117 with syringe locking mechanism 150. The result will be the separation of the aforementioned weak connection, leaving piston 103, separated from actuator rod 104, in the portion of the syringe below (or to the left in FIG. 1B) of syringe locking mechanism 150.

Once the seal between actuator rod 104 and piston 103 is broken, it is not possible to reattach or reconnect these two components which are located within cylinder 101. The prior art problem of a brute force being applied to pull the piston back past a locking mechanism utilizing a rod or plunger similar to actuator rod 104 is solved utilizing the invention since a brute force applied to actuator rod 104 while the piston is still attached will only serve to ensure the desired separation of the components once the assembly member 108 engages the syringe locking mechanism 150.

Reference should now be made to FIG. 2 which shows a simplified longitudinal cross-sectional view of the syringe system depicted in FIGS. 1A and 1B, with the flared safety cap removed and the piston shown partially depressed, i.e., with the syringe in use prior to the depicted locking mechanism engaging.

In particular, FIG. 2 depicts ring 210 and disc 215, actuator rod 204 and cylinder 201 which correspond to ring 110, disc 115, actuator rod 104 and cylinder 101 as shown in FIGS. 1A and 1B. Furthermore, FIG. 2 depicts piston 203 (shown comprises of piston members 203a and 203b together with assembly member 208), corresponding to piston 103 and the separately indicated assembly member 108 depicted in FIGS. 1A and 1B. Further yet, FIG. 2 depicts syringe locking mechanism 250, collar 216, rim 217, which correspond syringe locking mechanism 150, collar 116 and rim 117 as shown in FIGS. 1A and 1B.

Nubs 295 and 296 depicted in FIG. 2, referred to hereinbefore for supporting the snap lock flared safety cap feature of the invention, are shown on nozzle 216 into which syringe needle 260 may be inserted.

FIG. 2 also shows the location of the aforementioned weak attachment between actuator rod 204 and piston 203; namely at the junction 225 between these two components. Finally, FIG. 2 shows the "interconnection" between assembly member 208 and the rest of piston 203 (parts 203a and 203b) as a "dashed line" interconnection to indicate that, in some embodiments, the resilient material required for assembly member 208 may be used to form one integrated piston 203; while in alternate embodiments the parts 203a and 203b included in exemplary piston 203 may be fabricated utilizing other materials, such as a rigid plastic.

Parts 203a and 203b of piston 203 are shown as separate components in FIG. 2 to illustrate that, in accordance with a preferred embodiment of the invention, at least one other portion of piston 203 (in addition to the collar 216/rim 217 portion of piston 203) has a tendency to become flared and engage the cylinder walls; not for the purpose of cooperating with the syringe locking mechanism, but rather to help ensure that any fluids in well 185 (depicted in FIG. 1A) do not by-pass piston 203. This other portion of piston 203 is shown as additional collar 285 in FIG. 2. Furthermore, this preferred design will help to ensure that all fluid being dispensed via the syringe is forced out through the nozzle 216/needle 250 combination when the piston is depressed to the maximum limit achievable using the syringe system.

Figure 3:
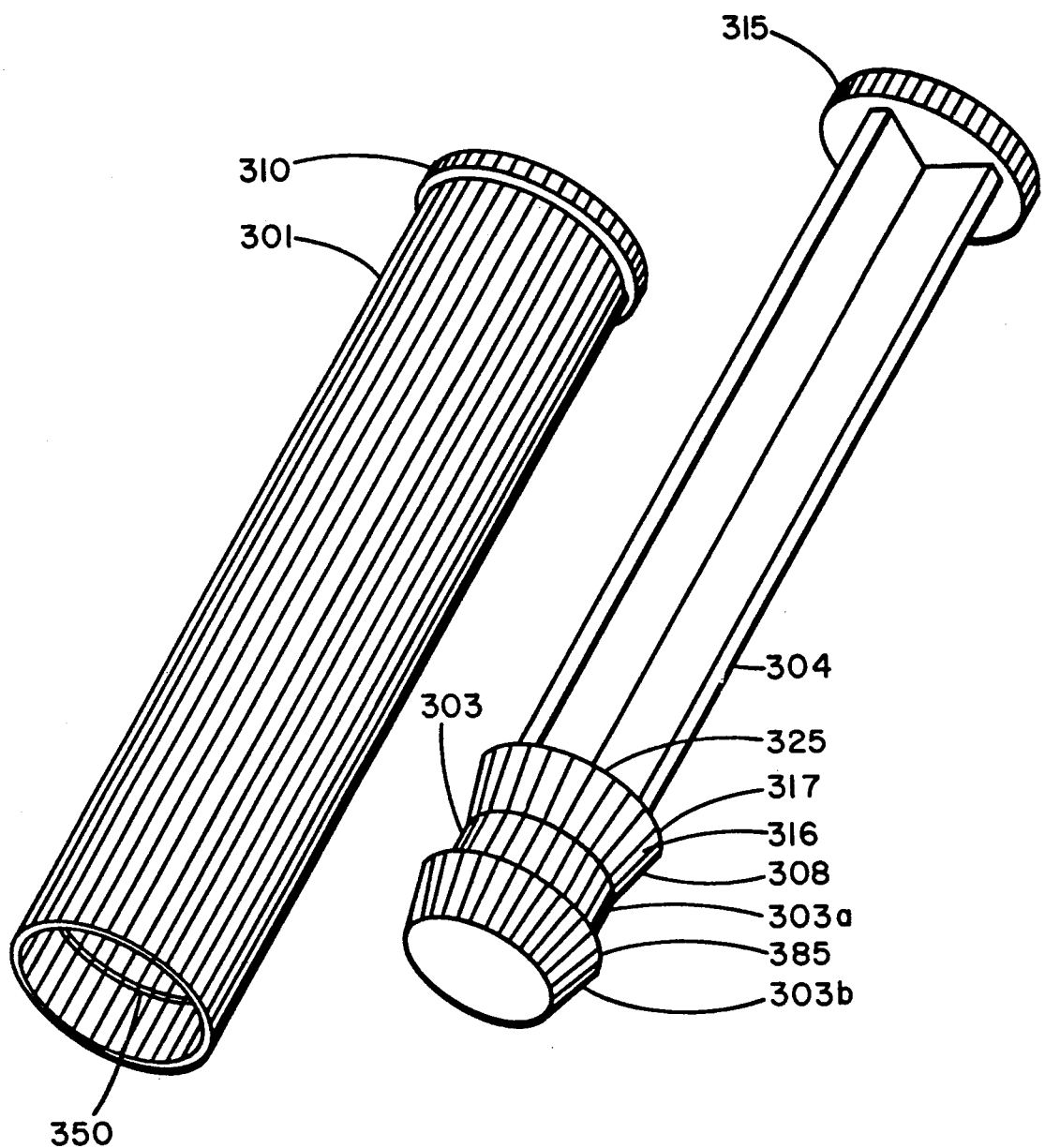
FIG. 3 illustrates in greater detail an embodiment of the component tubular (cylinder) portion of the syringe system depicted in FIG. 2, along with an exemplary actuator rod/piston combination as contemplated by the invention, which in FIG. 2 is shown inserted within the tubular portion of the syringe system.

Reference should now be made to FIG. 3 which illustrates in greater detail an embodiment of the component tubular (cylinder) portion of the syringe system depicted in FIG. 2, along with an exemplary actuator rod/piston combination as contemplated by the invention, which in FIG. 2 is shown inserted within the tubular portion of the syringe system. Thus, the component parts of a safety syringe system as contemplated by the invention (with the exception of a suitable cap which, as indicated hereinbefore, is suggested by the Masters, et al patent previously incorporated herein), are shown in FIG. 3.

In particular, cylinder 301 corresponds to cylinder 101 as shown in FIGS. 1A and 1B, the syringe locking mechanism depicted in FIGS. 1A and 1B is shown at 350 of FIG. 3, as a rim extending inwardly and around the inner portion of cylinder 350.

Ring 310 is shown formed on cylinder 301 and functions as ring 110 described hereinbefore with reference to FIGS. 1A and 1B. Likewise, disc 315 is shown on actuator rod 304 (corresponding to disc 115 and actuator rod 104 of FIGS. 1A and 1B); and the piston 303, shown with component parts 308, 303a and 303b, correspond to parts 203, 208, 203a and 203b respectively as described with reference to FIG. 2.

Finally, FIG. 3 shows a collar and peripheral rim portion (316 and 317 respectively) of assembly member 308, the preferred additional collar on piston 303 for preventing fluid leaks (collar 385), and the location of the weak attachment (the depicted illustrative point of direct connection 325) between piston 303 and actuator rod 304. These elements correspond to collar 216, rim 217, collar 285 and the connection 225 described hereinbefore with reference to FIG. 2.

What has been described in detail hereinabove are methods and apparatus meeting all of the aforestated objectives. As previously indicated, those skilled in the art will recognize that the foregoing description has been presented for the sake of illustration and description only. It is not intended to be exhaustive or to limit the invention to the precise from disclosed, and obviously many modifications and variations are possible in light of the above teaching.

The embodiments and examples set forth herein were presented in order to best explain the principles of the instant invention and its practical application to thereby enable others skilled in the art to best utilize the instant invention in various embodiments and with various modifications as are suited to the particular use contemplated.

It is, therefore, to be understood that the claims appended hereto are intended to cover all such modifications and variations which fall within the true scope and spirit of the invention.

What is claimed is:

1. A self-destructing disposable safety syringe system, suitable for preventing needle sticks, preventing syringe reuse, and dispensing fluids from, drawing fluids into and mixing fluids within said system, comprising:
  (a) a cylinder having a nozzle on one end to which a syringe needle can be affixed;
  (b) an at least partially resilient piston, suitable for sliding against the inside wall of said cylinder under the control of a force applied through an actuator rod attached to said piston, comprising a body arranged so as to form a liquid tight movable partition;
  (c) an actuator rod, connected to said piston via a weak attachment, for controlling the displacement of said piston within said cylinder by the application of forces through said actuator rod, wherein the weak attachment between said actuator rod and said piston is formed by directly coupling said actuator rod to said piston utilizing an adhesive sealant; and (d) a syringe locking mechanism, located on the inside wall of said cylinder and extending therein, arranged to permit the passage of said piston in the direction of said needle when forced in said direction by said actuator rod, wherein said syringe locking means is further arranged to engage and inhibit the passage of said piston in the direction away from said needle only once the entire piston has been forced past said syringe locking mechanism, thereby accommodating the dispensing the fluids from, drawing of fluids into and mixing of fluids within the syringe system until such time as said locking mechanism is engaged.

2. Apparatus as set forth in claim 1 wherein said system further includes means for locking said protective safety cap in a position covering said needle to prevent inadvertent cap removal and accidental needle sticks.

3. A self-destructing disposable safety syringe system, suitable for preventing needle sticks, preventing syringe reuse, and dispensing fluids from, drawing fluids into and mixing fluids within said system, comprising:

(a) a cylinder having a nozzle on one end to which a syringe needle can be affixed;

(b) an at least partially resilient piston, suitable for sliding against the inside wall of said cylinder under the control of a force applied though an actuator rod attached to said piston, comprising a body arranged so as to form a liquid tight movable partition;

(c) an actuator rod, directly connected to said piston via a weak attachment, for controlling the displacement of said piston within said cylinder by the application of forces through said actuator rod, wherein the direct weak attachment between said actuator rod and said piston is formed by coupling said actuator rod to said piston utilizing an adhesive sealant; and (d) a syringe locking mechanism, located on the inside wall of said cylinder and extending therein, operative to engage said piston once depressed beyond a predetermined distance upon any attempt to retract said piston and disconnect said weak attachment upon the exertion of a predetermined amount of force.

4. Apparatus as set forth in claim 3 wherein said syringe locking mechanism is arranged to permit the passage of said piston in the direction of said needle when forced in said direction by said actuator rod, and further arranged to engage and inhibit the passage of said piston in the direction away from said needle only once the entire piston has been forced past said syringe locking mechanism, thereby accommodating the dispensing of fluids from, drawing of fluids into and mixing of fluids within the syringe system until such time as said locking mechanism is engaged.

5. Apparatus as set forth in claim 3 further comprising a protective safety cap including a flared open end having a diameter that is greater than or equal to the body said cylinder.

6. Apparatus as set forth in claim 5 wherein said system further includes means for locking said protective safety cap in a position covering said needle to prevent inadvertent cap removal and accidental needle sticks.

7. Apparatus as set forth in claim 6 wherein said syringe locking mechanism is further comprised of a raised circumferential ridge which engages the back of the piston once depressed beyond a predetermined distance.

8. Apparatus as set forth in claim 7 wherein said raised circumferential ridge is tapered.

9. A self-destructing disposable safety syringe system, suitable for preventing needle sticks, preventing syringe reuse, and dispensing fluids from, drawing fluids into and mixing fluids within said system, wherein said system comprises:

(a) a cylinder having a nozzle on one end to which a syringe needle can be affixed;

(b) an at least partially resilient piston including a body arranged so as to form a liquid tight movable partition, suitable for sliding against the inside wall of said cylinder under the control of a force applied through an actuator rod attached to said piston;

(c) safety cap means, for preventing needle sticks from any needle attached to said nozzle, having a flared construction to ease the placement of said cap over said needle and further including a cap lock for preventing the accidental removal of said safety cap means once in place;

(d) syringe locking means, located on the interior wall of said cylinder and extending therein, for preventing the retraction of said piston once the piston is depressed beyond a certain predefined limit; and (e) means for causing the syringe to self destruct if any reuse attempt is made after said piston has been depressed beyond said predefined limit, wherein said means for causing said syringe to self-destruct is the combination of said piston and said actuator rod held fast by an adhesive sealant to form a direct weak connection therebetween.

10. Apparatus as set forth in claim 9 wherein said syringe locking means further comprises means for permitting the passage of said piston in the direction of said needle when forced in said direction by said actuator rod, and further wherein said syringe locking means is arranged to engage and inhibit the passage of said piston in the direction away from said needle only once the entire piston has been forced past said syringe locking mechanism, thereby accommodating the dispensing of fluids from, drawing of fluids into and mixing of fluids within the syringe system until such time as said locking mechanism is engaged.

11. A self-destructing disposable safety syringe system, suitable for preventing needle sticks, preventing syringe reuse, and dispensing fluids from, drawing fluids into and mixing fluids within said system, comprising:

(a) a tubular cylinder, forming a syringe barrel, one end of which includes a nozzle permitting an injection needle to be fixed thereon;

(b) an intake/delivery piston, including an assembly member forming an integral part of said piston, comprising a body forming a tight movable partition which is capable of sliding while maintaining the tightness along the inside wall of said tubular cylinder;

(c) an actuator rod, one end of which is disposed inside said cylinder and is directly attached to said assembly member via a weak connection to thereby allow the actuator rod/piston combination to be used to displace said piston in said cylinder by action applied to the actuator, wherein said weak connection is formed of an adhesive sealant which, upon the exertion of predetermined opposed forces on the connected rod and assembly member, causes said rod and assembly member to be separated; and (d) syringe locking means, located on the interior wall of said cylinder, for preventing the retraction of said piston once the piston is depressed beyond a certain predefined limit.

12. Apparatus as set forth in claim 11 wherein said assembly member has a free end that includes a first collar having a peripheral rim that has a tendency to bear against the inside wall of said cylinder.

13. Apparatus as set forth in claim 12 wherein said piston includes a second collar that has a tendency to bear against the inside wall of said cylinder to prevent fluid leaks.

14. Apparatus as set forth in claim 12 wherein said syringe locking means comprises a ridge of material extending inwardly and around the interior of said cylinder for engaging said rim after the entire piston passes the portion of said cylinder where said syringe locking mechanism is located.

15. Apparatus as set forth in claim 12 wherein said syringe locking means comprises a set of locking teeth extending into the interior of said cylinder for engaging said rim after the entire piston passes the portion of said cylinder where said syringe locking mechanism is located.

16. Apparatus as set forth in claim 14 wherein said syringe locking mechanism is fabricated within said cylinder at a predetermined location which would allow the syringe to be utilized for mixing fluids, as well as dispensing fluids, prior to said rim being engaged by said locking means.

17. Apparatus as set forth in claim 11 wherein said piston is formed utilizing a resilient material.

18. Apparatus as set forth in claim 17 wherein said resilient material consists essentially of a synthetic plastic that ensures a tight fit and accommodates a sliding action between the said piston and the inside wall of said cylinder.

19. Apparatus as set forth in claim 11 wherein said assembly member portion of said piston is formed utilizing a resilient material.

20. Apparatus as set forth in claim 11, further comprising means for causing the syringe to self destruct if any reuse attempt is made after said piston has been depressed beyond said predefined limit, wherein said means for causing said syringe to self-destruct is the combination of said piston and said actuator rod held fast by said sealant.

* * * * *